United States Patent [19]

Kunitz et al.

[11] 4,186,019
[45] Jan. 29, 1980

[54] COLOR PHOTOGRAPHIC MATERIAL CONTAINING NOVEL 2-EQUIVALENT YELLOW COUPLERS

[75] Inventors: Friedrich-Wilhelm Kunitz; Heinz Salzmann, both of Leverkusen, Fed. Rep. of Germany

[73] Assignee: Agfa-Gevaert Aktiengesellschaft, Fed. Rep. of Germany

[21] Appl. No.: 907,184

[22] Filed: May 18, 1978

[30] Foreign Application Priority Data

May 24, 1977 [DE] Fed. Rep. of Germany ....... 2723301

[51] Int. Cl.$^2$ ................................................ G03C 1/40
[52] U.S. Cl. ..................................... 430/557; 430/389
[58] Field of Search .................. 96/100 R, 56, 55, 56.6

[56] References Cited
U.S. PATENT DOCUMENTS

| | | | |
|---|---|---|---|
| 4,009,038 | 2/1977 | Arai et al. | 96/56 |
| 4,021,248 | 5/1977 | Shiba et al. | 96/100 R |
| 4,021,428 | 5/1977 | Furutachi et al. | 96/100 R |

Primary Examiner—J. Travis Brown
Attorney, Agent, or Firm—Connolly & Hutz

[57] ABSTRACT

Useful 2-equivalent yellow couplers correspond to the formula

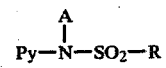

in which
  A represents a yellow coupler radical connected through the coupling position
  Py represents a pyridine group connected to the N through one of its carbon atoms
  R represents alkyl, aryl or dialkylamino The couplers provide high color density and low color fog.

1 Claim, No Drawings

COLOR PHOTOGRAPHIC MATERIAL CONTAINING NOVEL 2-EQUIVALENT YELLOW COUPLERS

This invention relates to a photographic material containing novel 2-equivalent yellow couplers.

It is known to produce coloured photographic images by chromogenic development i.e. a process in which silver halide emulsion layers which have been exposed imagewise are developed by means of suitable colour producing developer substances, so-called colour developers, in the presence of suitable colour couplers so that the oxidation product formed from the developer substances in accordance with the silver image reacts with the colour coupler to form a dye image. The colour developers used are generally aromatic compounds containing primary amino-groups, in particular those based on p-phenylene diamine.

For subtractive three-colour photography, there is generally used a light sensitive photographic multilayer material containing a red-sensitized, a green-sensitized and a blue-sensitive silver halide emulsion layer in which a cyan, a magenta and a yellow dye image, respectively, are formed by colour development in the presence of suitable colour couplers.

The conventional yellow couplers contain an active methylene group which reacts with the oxidised colour developer during development. This reaction requires four equivalents of developable silver halide. These couplers are therefore known as four-equivalent couplers. Other couplers are known, in which a hydrogen from the active methylene group is substituted by a group which can be split off in the coupling reaction. In such a case, only two equivalents of developable silver halide are required for forming the dye. These couplers are therefore known as two-equivalent couplers. The following are examples of groups which can be split off:

Halogen, alkoxy, aroxy, thioether groups and saturated or unsaturated heterocyclic rings in many cases containing keto groups, which rings are attached to the coupling position through a ring nitrogen atom.

The advantage of 2-equivalent couplers compared with 4-equivalent couplers is that they require about half the quantity of silver halide to form a given quantity of dye. Apart from the saving in silver, this means that the emulsion layer can be cast more thinly, which is advantageous for the resolution and sharpness of the photographic material.

Among the 2-equivalent couplers known in the art which have the splitable groups mentioned above, 2-equivalent yellow couplers containing halogen as removable group have proved to be particularly suitable in practice since for colour development of a photographic material the reactivity of the 2-equivalent yellow couplers must be sufficiently high to ensure that adequate colour densities will be obtained within even short processing times.

In practice, however, 2-equivalent yellow couplers which contain fluorine as splitable group have failed to become established because of difficulties in preparation. 2-equivalent yellow couplers containing chlorine as splitable group, on the other hand, frequently have a harmful effect on the photographic properties of the silver halide emulsion. As has been described in German Offenlegungsschrift No. 2,114,577, only certain yellow couplers based on benzoyl acetanilide, containing chlorine as splitable group are photographically relatively inert and have only a slight influence on the formation of colour fog during development. However, the aforesaid couplers do not meet all of the photographic requirements in that if the unprocessed photographic material is stored under warm, moist conditions, an increase in fogging during development may occur.

There have been many attempts in practice to find new two-equivalent yellow couplers which are easily prepared and are sufficiently reactive for colour photographic development. The known two-equivalent yellow couplers, however, still do not satisfy the requirements in this respect.

Another problem is that it must be possible for two-equivalent couplers to be introduced in finely divided form into the hydrophilic colloid layers of photographic materials without crystallizing out or in any other way harmfully affecting the photographic or mechanical properties of the layer.

In addition, two-equivalent couplers must be sufficiently stable when photographic materials containing them are stored at elevated temperatures or under moist, warm conditions so that the splitable group will not be split off before chromogenic development. At the same time, this group must be easily and completely split off in the process of chromogenic development if high colour saturation and sufficient sensitivity are to be achieved. These properties must, of course, be independent of the methods employed for introducing the couplers into the hydrophilic colloid layers. Hydrophobic couplers which are resistant to diffusion are either introduced into the layer in an alkali soluble form, which is achieved by the introduction of solubilizing groups, or they are dissolved in an organic solvent and then emulsified in the gelatine solution, in known manner, if indicated with the addition of oily coupler solvents.

The reactivity of the couplers depends to some extent on the method employed for preparing the emulsion. If sufficiently highly reactive two-equivalent couplers are to be obtained, the hydrophilic colloid layer and/or the more hydrophobic oil droplets must have a solvating effect to assist the splitting off of the splitable group during chromogenic development.

This removable group must, of course, be photographically inert and must have no harmful effect on the dyes formed or on the stability of unused residual coupler in the layer.

It is an object of this invention to provide easily prepared novel 2-equivalent yellow couplers which are suitable for use in light sensitive materials for the production of yellow partial images and which are superior in their properties to the couplers known in the art.

A light sensitive material containing at least one silver halide emulsion layer and a diffusion resistant two-equivalent yellow coupler of the following formula:

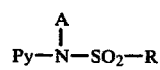

has now been found, in which formula

A represents the group left after removal of a hydrogen atom from the activated methylene group of a four-equivalent yellow coupler;

Py represents a pyridine group which may contain one or more substituents;

R represents alkyl with preferably 1 to 10 carbon atoms, more preferably 1 to 4 carbon atoms, in particular methyl, which may be substituted, e.g. with halogen, hydroxyl, alkoxy or acyl; dialkylamino, for example dimethylamino; or aryl, in particular phenyl, which may be substituted, e.g. with alkyl, alkoxy halogen and/or nitro.

The group A may in particular represent the group of a yellow coupler represented by the following formula:

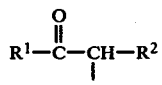

in which
R$^1$ represents
(1) an alkyl group with 1 to 32 carbon atoms which may be substituted, in particular a branched alkyl group in which a secondary or tertiary carbon atom is preferably directly attached to the carbonyl group, in particular a tert.-butyl-group,
(2) alkoxyalkyl,
(3) cycloalkyl,
(4) a heterocyclic group or
(5) aryl, in particular phenyl, which may have one or more substituents, e.g. halogen, alkoxy or acylamino, alkyl, aroxy, hydroxy, alkylamino or dialkylamino;
R$^2$ represents a group represented by the following formula:

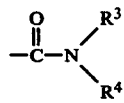

in which
R$^3$ represents a short chain alkyl groups, preferably of up to 4 carbon atoms or, what is preferred, hydrogen,
R$^4$ represents (1) alkyl with 1 to 18 carbon atoms or (2) what is preferred, aryl in particular phenyl, which may be substituted with one or more of the same or different groups, e.g. with an alkyl group having 1 to 18 carbon atoms, aryl e.g. phenyl, aralkyl, e.g. benzyl, aroxy e.g. phenoxy, or in particular halogen e.g. chlorine or bromine, sulfo, carboxyl, acyl, acyloxy or acylamino in which the said acyl groups may be derived from aliphatic or aromatic carboxylic or sulphonic acids or from carbonic acid mono-esters, carbamic acids or sulfamic acids.

The pyridine group represented by Py is attached to the nitrogen atom of the above formula through one of its ring carbon atoms, preferably through a carbon atom in the o-position. The substituents on the pyridine group may be, in particular chlorine or alkyl, e.g. methyl.

By suitable choice of the substituents R$^1$ or R$^4$, the yellow couplers according to the invention may be provided with at least one diffusion conferring group, e.g. a straight or branched chain alkyl group containing 10 to 18 carbon atoms, or they may be substituted with alkyl substituted phenoxy groups which may be attached either directly or indirectly, for example through —O—, —S—, —CONH—, —NHCO—, —SO$_2$NH—, —NHSO$_2$— or other intermediate members to at least one of the groups R$^1$ and R$^4$, which may be aromatic groups. If the compounds are required to be soluble in alkalis, at least one of the groups R$^1$ and R$^4$ may carry groups which confer solubility in alkalis, preferably sulfo groups. Examples of suitable yellow couplers according to the invention are described below.

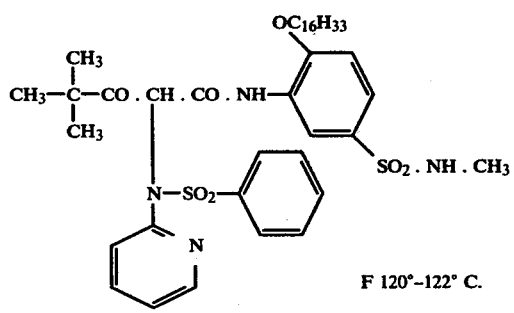

1.

F 120°–122° C.

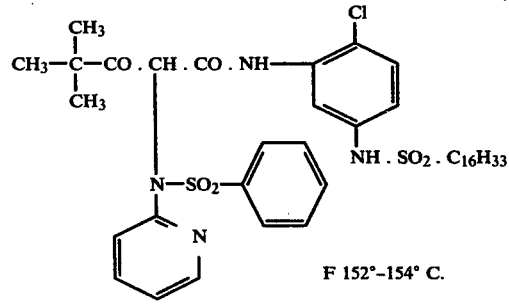

2.

F 152°–154° C.

-continued
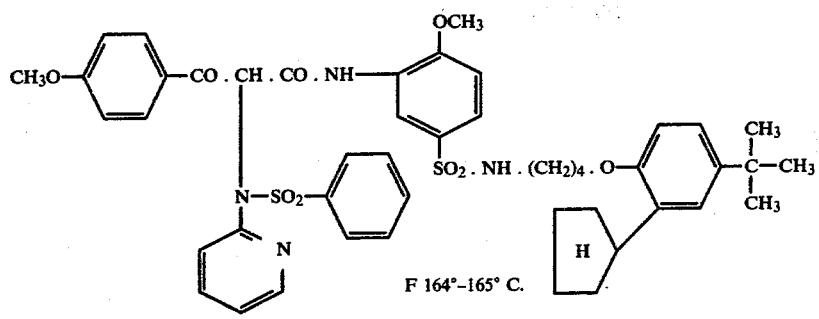
3.
F 164°–165° C.
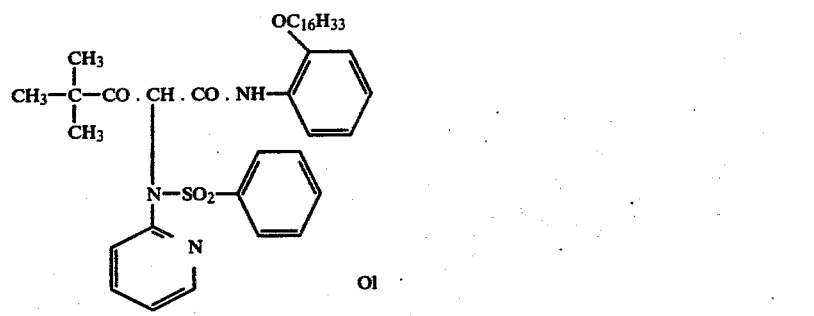
4.
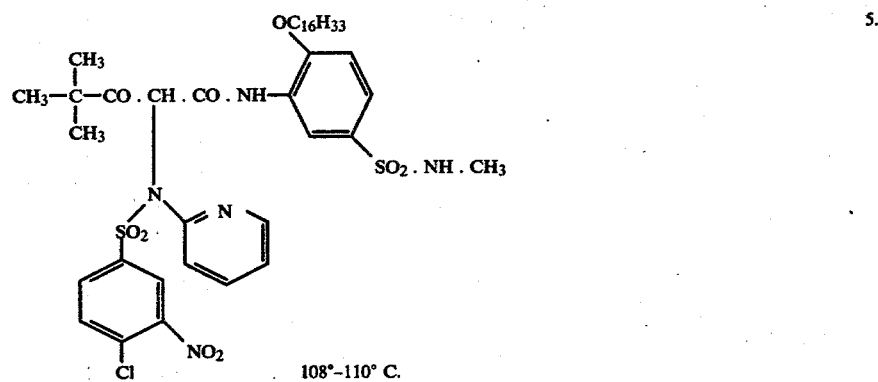
5.
108°–110° C.
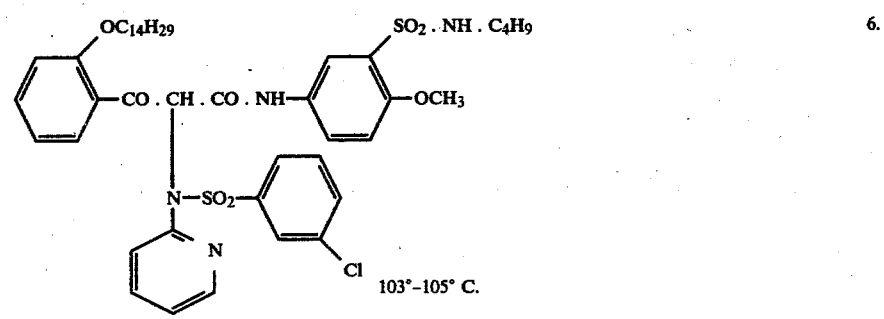
6.
103°–105° C.
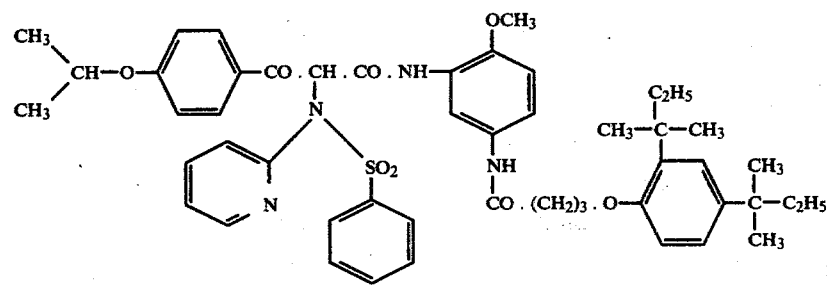
7.
F 149°–151° C.

-continued
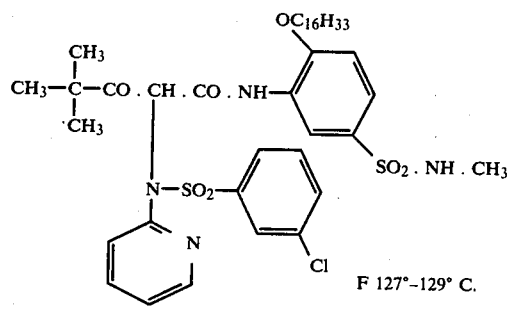
8.
F 127°-129° C.
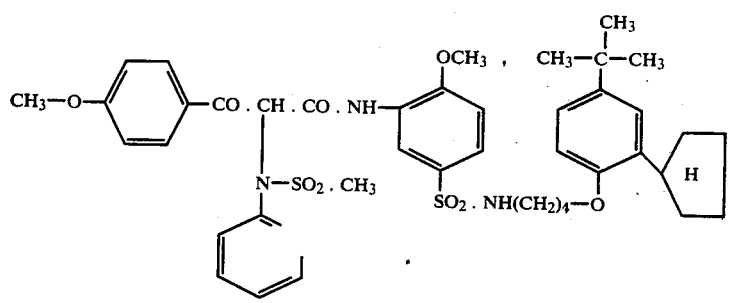
9.
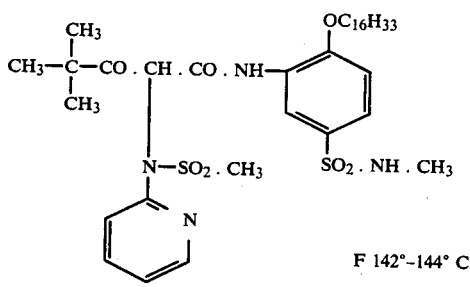
10.
F 142°-144° C.
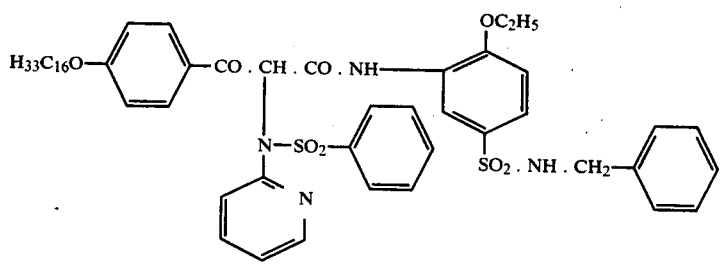
11.
F 127°-129° C.
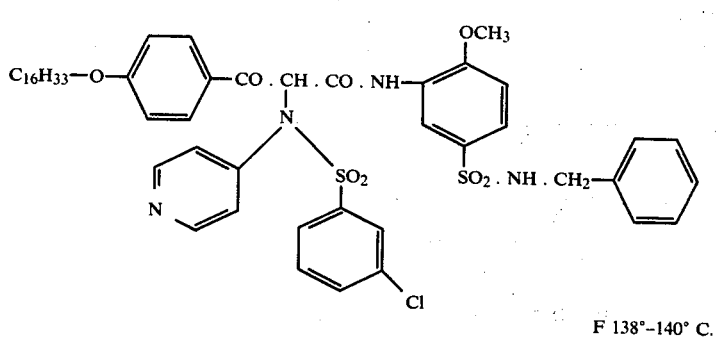
12.
F 138°-140° C.

The reaction also proceeds very favourably in the presence of hexamethyl phosphoric acid triamide as solvent, which has the added effect of accelerating the reaction, as described in German Offenlegungsschrift No. 2,329,587.

The α-Cl-substituted couplers and the α-Br-substituted couplers may be prepared by the method described in U.S. Pat. No. 2,728,658 or by reacting a corresponding α-unsubstituted compound with N-bromosuccinimide.

The couplers according to the invention may also be prepared from 4-equivalent couplers by the one-stage synthesis described in German Offenlegungsschrift No. 2,545,756.

The preparation of coupler 1 is described below; the other couplers according to the invention are prepared in similar manner.

COUPLER 1

(a) 2-phenylsulfonylaminopyridine

A solution of 264 g of benzene sulphochloride was added dropwise at 10° to 25° C. to a solution of 282 g of 2-aminopyridine in 1200 ml of tetrahydrofuran. After two hours continuous stirring without further cooling, the mixture was poured into water. The reaction product was suction filtered and washed first with water and then with methanol.

Yield: 216 g; m.p. 174°–175° C.

(b) Coupler 1

12.2 g (1/50 mol) of α-pivaloyl-α-bromo-(2-cetyloxy-5-N-methyl-sulfamoyl)-acetanilide were introduced portionwise into a mixture of 4 g (1/00 mol) of 2 phenyl-sulphonylaminopyridine, 100 ml of hexamethyl phosphoric acid triamide and 3 ml of N,N,N',N'-tetramethylguanidine at room temperature.

The whole mixture was then stirred for one hour, and poured into cold, dilute hydrochloric acid. The precipitate was suction filtered and washed with water. The moist filter cake was taken up in ethyl acetate and the solution was washed with water until neutral, dehydrated with sodium sulphate and concentrated by evaporation. Recrystallization of the crude product from ethanol yielded 5.2 g of chromatographically pure coupler 1 melting point 120°–122° C.

When preparing the light-sensitive colour photographic material according to the invention, the diffusion resistant yellow couplers may be incorporated in known manner in the casting solution of the silver halide emulsion layers or other colloid layers. For example, water soluble colour couplers, i.e. those which have one or more water solubilizing groups such as a sulfo or carboxyl group (in acid or salt form) may be added to a hydrophilic colloid solution from an aqueous solution whereas colour couplers which are insoluble or insufficiently soluble in water may be added from a solution in a suitable water-miscible or water immiscible high boiling organic solvent or mixtures of such solvents in the presence of a wetting agent or a dispersing agent. In addition to containing the binder, the hydrophilic casting solution may, of course, also contain other conventional additives. Water insoluble colour couplers which contain flourosulphonyl groups or carboxylic acid ester groups such as ethoxycarbonyl groups may also be converted into the corresponding sulphonic acids or carboxylic acids or their alkali metal salts by alkaline hydrolysis and then added from aqueous solutions.

The solution of colour coupler need not be dispersed directly in the casting solution for the silver halide emulsion layer or another water permeable layer associated to the silver halide emulsion layer buty may advantageously first be dissolved or dispersed in an aqueous, light-insensitive solution of a hydrophilic colloid and the resulting mixture may then be mixed with the casting solution for the light-sensitive silver halide emulsion layer or some other water permeable layer, optionally after removal of the organic solvent used, and the mixture may then be applied. Further details about suitable techniques for incorporating colour couplers into the hydrophilic colloid layers of a photographic material may be found in published Dutch Patent application Nos. 6,516,423; 6,514,424; 6,600,098; 6,600,099; and 6,600,628 and in Belgian Pat. No. 750,889; U.S. Pat. No. 2,304,940 and British Pat. No. 791,219.

To produce photographic colour images, an exposed silver halide emulsion layer is developed with an aromatic primary amino developer substance in the presence of a colour coupler according to the invention. The developer substances used may be any colour developer substances which, when in the form of their oxidation product, are capable of reacting with the colour coupler to form azomethine dyes. Suitable developer substances include aromatic compounds such as p-phenylamine diamine and its derivatives, for example, N,N-dialkyl-p-phenylene-diamine such as N,N-diethyl-p-phenylene diamine, 1-(N-ethyl-n-methane-sulphon-amido-ethyl-) 3-methyl-p-phenylene diamine; 1-(N-ethyl-N-hydroxyethyl)-3-methyl-p-phenylene diamine and 1-(N-ethyl-N-methoxyethyl)-3-methyl-p-phenylene diamine.

The light sensitive silver halide emulsions may be emulsions of silver chloride, silver bromide or mixtures thereof, which may have a small silver iodide content of up to 10 mol%, in one of the usual hydrophilic binders. The binder used for the photographic layers is preferably gelatine but this may be partly or completely replaced by other natural or synthetic binders. Suitable natural binders include e.g. alginic acid and its derivatives such as its salts, esters or amides, cellulose derivatives such as carboxymethyl cellulose, alkyl celluloses such as hydroxyethyl cellulose, starch or its derivatives such as its ethers or esters, or carragheenates. Polyvinyl alcohol, partially saponified polyvinyl acetate, and polyvinyl pyrrolidone are examples of suitable synthetic binders.

The emulsions may also be chemically sensitized, for example by the addition of sulphur compounds such as allyl isothiocyanate, allyl thiourea or sodium thiosulphate at the chemical ripening stage. Reducing agents, e.g. the tin compounds described in the Belgian Pat. Nos. 493,464 and 568,687, polyamines such as diethylene triamine or aminomethane sulphinic acids derivatives, e.g. according to Belgian Pat. No. 547,323, may also be used as chemical sensitizers. Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65–72 (1951). The chemical sensitizers mentioned above may also be used in combination with each other.

The emulsions may also be sensitized with polyalkylene oxide derivatives, e.g. with a polyethylene oxide having a molecular weight of between 1,000 and 20,000 or with condensation products of alkylene oxides and -continued

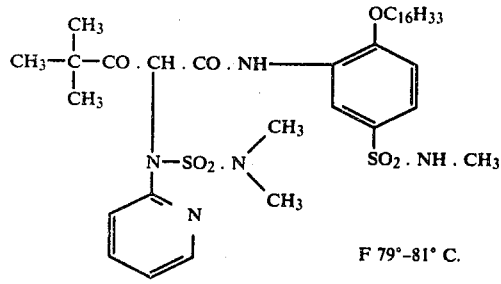

F 79°-81° C.

13.

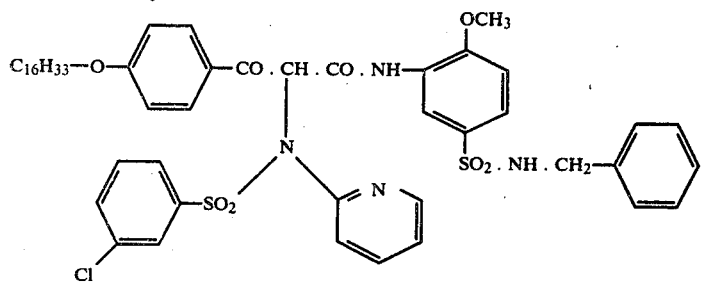

F 120°-122° C.

14.

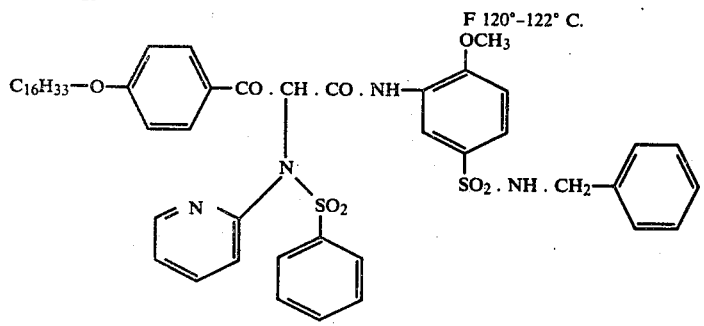

F 123°-125° C.

15.

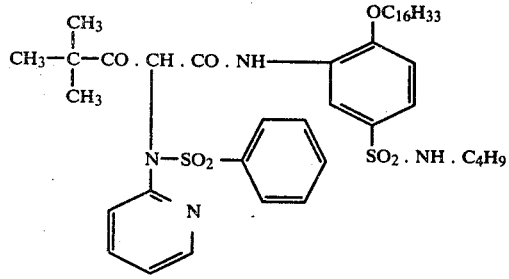

F 90°-91° C.

16.

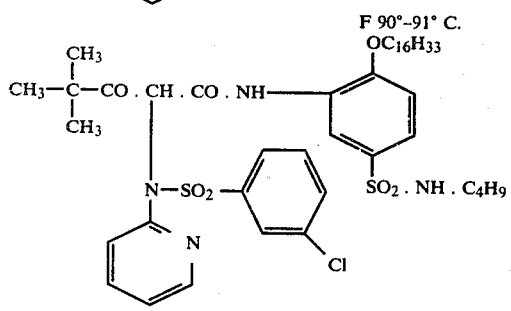

F 108°-110° C.

17.

The yellow couplers according to the invention may be prepared by reacting the corresponding 2-equivalent couplers which contain chlorine or bromine as splitable group with the corresponding alkylsulfonyl-, arylsulfonyl- or dialkylaminosulfonyl-aminopyridine in the presence of a base by the usual method, e.g. as described in German Offenlegungsschrift No. 2,213,461. The reaction may be carried out in an aprotic, preferably polar, solvent such as acetonitrile or dimethylformamide. Suitable basic compounds include open chain or cyclic amines, e.g. pyridine or alkyl metal salts of alcoholates, e.g. sodium alcoholate.

aliphatic alcohols, glycols, cyclic dehydration products of hexitols, alkyl-substituted phenols, aliphatic carboxylic acids, aliphatic amines, aliphatic diamines and amides. The condensation products have a molecular weight of at least 700, preferably more than 1000. These sensitizers may, of course, be combined in order to obtain special effects, as described in Belgian Pat. No. 537,278 and British Pat. No. 727,982.

The emulsions must be sufficiently sensitive in the blue spectral region. Unsensitized emulsions the sensitivity of which is due to the intrinsic sensitivity of the silver halides are generally used for this purpose but it is also possible to sensitize the silver halide emulsions to the blue region of the spectrum, e.g. by means of sensitizers such as those described in German Offenlegungsschrift No. 1,808,041.

The emulsions may contain the usual stabilizers, e.g. homopolar compounds or salts of mercury containing aromatic or hetercyclic rings, such as mercaptotriazoles, simple mercury salts, sulphonium mercury double salts and other mercury compounds. Azaindenes are also suitable stabilizers particularly tetra- and penta-azaindenes, especially those which are substituted with hydroxyl or amino groups. Compounds of this kind have been described in the article by Birr, Z. Wiss. Phot, 47, 2–27 (1952). Other suitable stabilizers include heterocyclic mercapto compounds, e.g. phenyl mercaptotetrazole, quarternary benzothiazole derivatives and benzotriazole.

The emulsions may be hardened in the usual manner, for example with formaldehyde or halogen-substituted aldehydes which contain a carboxyl group, such as mucobromic acid, diketones, methane sulphonic acid esters and dialdehydes and the like.

The photographic layers may also be hardened with epoxy hardeners, heterocyclic ethylene imine hardeners or acryloyl hardeners. Examples of such hardeners have been described, for example, in German Offenlegungsschrift No. 2,263,602 and British Pat. No. 1,266,655. The layers may also be hardened by the process according to German Offenlegungsschrift No. 2,218,009 in order to obtain colour photographic materials which are suitable for high temperature processing.

The photographic layers or colour photographic multilayered materials may also be hardened with diazine, triazine or 1,2-dihydroquinoline hardeners ad described in British Pat. Nos. 1,193,290; 1,251,091; 1,306,544 and 1,266,655, French Pat. No. 7,102,716 and German Offenlegungsschrift No. 2,332,317. Examples of such hardeners include diazine derivatives containing alkyl-sulphonyl or aryl-sulphonyl groups, derivatives of hydrogenated diazines or triazines such as 1,3,5-hexahydrotriazine, fluoro-substituted diazine derivatives such as fluoropyrimidines or esters of 2-substituted 1,2-dihydroquinoline- or 1,2-dihydroisoquinoline-N-carboxylic acids. Vinyl sulphonic acid hardeners, carbodiimide hardeners and carbomyl hardeners may also be used, e.g. those described in German Offenlegungsschrift Nos. 2,263,602; 2,225,230 and 1,808,685, French Pat. No. 1,491,807, German Pat. No. 972,153 and East German Pat. No. 7,218. Other suitable hardeners have been described in, for example, British Pat. No. 1,268,550.

Suitable wetting agents which may be used according to the invention for incorporating the couplers have been described by Gerhard Gewalek in "Wasch- und Netzmittel", Akademie-Verlag Berlin (1962). Examples include the sodium salts of N-methyl-oleyltauride, sodium stearate, the sodium salt of heptadecenyl-benzimidazole sulphonic acid, sodium sulphonates of higher aliphatic alcohols, e.g. 2-methyl-hexanol-sodium sulphonate, sodium-diiso-octylsulphosuccinate, sodium dodecyl sulphonate and the sodium salt of tetradecylbenzene sulphonic acid. Partially fluorinated or perfluorinate alkane carboxylic or alkane sulphonic acids or their amides are also suitable.

The materials according to the invention may be used for various purposes, e.g. as positive, negative or reversal materials.

The usual substrates which are used in known manner for the preparation of photographic materials are suitable, e.g. foils of cellulose nitrate, cellulose acetate such as cellulose triacetate, polystyrene, polyesters such as polyethylene terephthalate, polyolefines such as polyethylene or polypropylene, baryta paper substrates and polyolefine-laminated, e.g. polyethylene laminated paper substrates and glass.

The advantageous properties of the couplers according to the invention are described below with the aid of Examples.

EXAMPLE (1) 2 mols of coupler No. 2 were dissolved in 3 ml of ethyl acetate and emulsified in known manner in 20 ml of a 5% gelatine solution after the addition of 0.5 g of dibutyl phthalate at 60° C. The emulsion contained 0.16 g of dodecyl benzene-sulphonic acid sodium.

The emulsion was then mixed with 85 g of a 7.5% gelatine solution which contained 1.93 g of silver bromide in the dispersed form, and the mixture was diluted with water to the required casting viscosity.

After it had been poured on a transparent support layer of cellulose triacetate, the material prepared as described above was exposed behind a grey step wedge and cut up into several samples.

One sample was processed fresh, another sample was kept in a heating cupboard at 57° C. and 34% relative humidity for seven days before photographic processing. The samples were developed in a colour developer which contained the following substances per liter:

| 4 g | sodium hexamethaphosphate | |
|---|---|---|
| 1.2 g | hydroxylamine hydrochloride | |
| 2.75 g | N' N'-diethylamino-p-phenylene diamine | |
| 2 g | sodium sulphite | |
| 75 g | potassium carbonate | |
| 2.5 g | potassium bromide | |
| Processing at 20° C.: | | |
| Development: | | 8 min. |
| Washing: | | 15 min. |
| Colour negative bleaching bath: | | 5 min. |
| Washing: | | 5 min. |
| Fixing bath: | | 5 min. |
| Washing: | | 10 min. |

Materials were similarly prepared from couplers Nos. 3 and 5 and from a comparison coupler A and processed. The comparison coupler was a compound represented by the following formula:

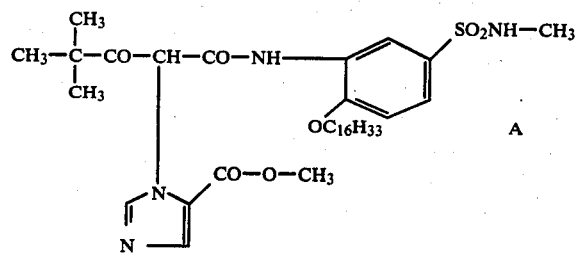

The results obtained are shown in the following table:

| Coupler | ΔS | E | γ | Dmax |
|---|---|---|---|---|
| A | +18 | — | 1.6 | 2.4 |
| 2 | +6 | −1.3 | 1.05 | 2.6 |
| 3 | +7 | −1.3 | 1.2 | 2.8 |
| 5 | +4 | −2.3 | 1.25 | 2.5 |

ΔS represents the increase in fog (in 1/100 density units) after storage in the heating cupboard;
E represents the relative sensitivity of the freshly processed sample in 1/10 log.I.t. units measured at density 0.2 above fog.
Coupler A was used for comparison.

It can be seen that at comparable sensitivity, the couplers according to the invention are superior to the comparison couplers in the maximum density. At the same time, they produce considerably less fogging in the heating cupboard.

Another sample from each of the materials described above was developed in a colour developer containing the following additives (per liter):

| | |
|---|---|
| 3 g | benzyl alcohol |
| 2 g | sodium sulphate sicc |
| 5 ml | sodium hydroxide (10%) |
| 50 g | sodium carbonate sicc |
| 1 g | potassium bromide |
| 5 g | N'-ethyl-N'-β-methylsulphonylaminoethyl-2-methyl-p-phenylene diamine |
| 2 g | Sodium hexametaphosphate. |

Processing at 20° C.:

| | |
|---|---|
| Development: | 12 min. |
| Washing: | 15 min. |
| Colour negative bleaching bath: | 5 min. |
| Washing: | 5 min. |
| Fixing bath: | 5 min. |
| Washing: | 10 min. |

The results are shown in the following table:

| coupler | sensitivity | γ | Dmax |
|---|---|---|---|
| A | — | 1.0 | 1.9 |
| 2 | −2.6 | 0.8 | 2.1 |
| 3 | −1.6 | 0.96 | 2.5 |
| 5 | −3.0 | 0.95 | 2.0 |

We claim:

1. Light sensitive material comprising at least one silver halide emulsion layer and in said silver halide emulsion layer or in a non-light-sensitive binder layer 2-equivalent yellow coupler which contains, in the coupling position, a nitrogen-containing group which can be split off in the coupling reaction, wherein the improvement comprises the 2-equivalent coupler is a compound represented by the following formula:

$$Py-\underset{\underset{}{|}}{N}-SO_2-R$$
$$\overset{A}{|}$$

in which

A represents the group remaining after removal of a hydrogen atom from the activated methylene group of a 4-equivalent yellow coupler and corresponding to the formula $$R^1-\overset{O}{\underset{\|}{C}}-\underset{|}{CH}-R^2$$

Py is a pyridine group connected to the N through one of its carbon atoms;
R represents alkyl with 1 to 10 carbon atoms, dialkylamino or aryl.
$R^1$ represents alkyl with 1 to 32 carbon atoms, alkoxyalkyl, cycloalkyl, or aryl
$R^2$ represents the group $$-CO-N\underset{R^4}{\overset{R^3}{<}}$$

$R^3$ represents hydrogen or alkyl with up to 4 carbon atoms
$R^4$ represents alkyl with 1 to 18 carbon atoms or aryl which may be substituted with one or more substituents selected from the group consisting of alkyl, aryl, aralkyl, aroxy, halogen, sulfo, carboxyl, acyl, acyloxy and acylamino.

* * * * *